United States Patent [19]

Collins et al.

[11] Patent Number: 5,434,185

[45] Date of Patent: Jul. 18, 1995

[54] METHOD FOR INHIBITING ANGIOGENESIS WITH AURINTRICARBOXYLIC ACID, ITS ANALOGUES OR SALTS

[75] Inventors: Delwood C. Collins; Antonio Gagliardi; Anjan Bhattacharyya, all of Lexington, Ky.

[73] Assignee: The University of Kentucky Research Foundation, Lexington, Ky.

[21] Appl. No.: 61,477

[22] Filed: May 17, 1993

[51] Int. Cl.$^6$ .............................................. A61K 31/19
[52] U.S. Cl. .................................................. 514/570
[58] Field of Search ................. 514/159, 557, 150, 570

[56] References Cited

U.S. PATENT DOCUMENTS

| | | | |
|---|---|---|---|
| 4,007,270 | 2/1977 | Bernstein et al. | 514/159 |
| 4,113,879 | 9/1978 | Jones et al. | 514/522 |
| 4,749,647 | 6/1988 | Thomas et al. | 435/5 |
| 4,880,788 | 11/1989 | Moake et al. | 514/150 |
| 5,045,467 | 9/1991 | Bertheussen | 435/240.31 |

OTHER PUBLICATIONS

Benezra, Miriam, et al. "Reversal of Basic Fibroblast Growth Factor–mediated Autocrine Cell Transformation by Aromatic Anionic Compounds", Cancer Research, vol. 52, (Oct. 15, 1992) pp. 5656–5662.

Bouck, N. "Tumor Angiogenesis: The Role of Oncogenes and Tumor Suppressor Genes", Cancer Cells, vol. 2, No. 6, (Jun. 1990) pp. 179–185.

Cushman, M. et al. "Preparation and Anti–HIV Activities of Aurintricarboxylic Acid Fractions and Analogues: Direct Correlation of Antiviral Potency with Molecular Weight", J. Med. Chem., vol. 34, (1991) pp. 329–337.

Cushman, M. et al., "Synthesis and Anti–HIV Activities of Low Molecular Weight Aurinitricarboxylic Acid Fragments and Related Compounds", J. Med. Chem., vol. 34, (1991) pp. 337–342.

Folkman, J. et al., "Angiogenic Factors", Science, vol. 235, (1987) pp. 442–447.

Folkman, J. et al. "Angiogenesis Inhibition and Tumor Regression Caused by Heparin or a Heparin Fragment in the Presence of Cortisone", Science, vol. 221, (Aug. 19, 1983) pp. 719–725.

Gagliardi, A. et al. "Inhibition of Angiogenesis by Suramin", Cancer Research, vol. 52, (Sep. 15, 1992) pp. 5073–5075.

Gonzalez, R .G. et al. "Fractionation and Structural Elucidation of the Active Components of Aurintricarboxylic Acid, a Potent Inhibtior of Protein Nucleic Acid Interactions". Biochimica et Biophysica Acta, vol. 562, (1979) pp. 534–545.

Kan, M. et al. "An Essential Heparin-binding Domain in the Fibroblast Growth Factor Receptor Kinase", Science, vol. 259, (Mar. 26, 1993) pp. 1918–1921.

Klagsbrun, M. et al. "Minireview: A Dual Receptor System is Required for Basic Fibroblast Growth Factor Activity", Cell, pp. 229–231 (1991).

Mellon, W. S. "Inhibitory Action of Aurintricarboxylic Acid and Rifamycin AF/013 at the Polynucleotide Domain of 1,25-Dihydroxyvitamin $D_3$–Receptor Complexes", Biochemical Pharmacology, vol. 33, No. 7, (1984) pp. 1047–1057.

Moudgil, V. K. et al. "Modulation of DNA Binding of Glucocorticoid Receptor by Aurintricarboxylic Acid", J. Steroid Biochem., vol. 23, No. 2, (1985) pp. 125–132.

Nakane, H. et al. "Differential Inhibition of various Deoxyribonucleic Acid Polymerases by Evans Blue and Aurintricarboxylic Acid", Eur. J. Biochem., vol. 177, (1988) pp. 91–96.

Oikawa, T. et al. "A Highly Potent Antiangiogenic Activity of Retinoids", Cancer Letters, vol. 48, (1989) pp. 157–162.

(List continued on next page.)

Primary Examiner—Marianne M. Cintins
Assistant Examiner—K. Weddington
Attorney, Agent, or Firm—Lowe, Price, LeBlanc & Becker

[57] ABSTRACT

Aurintricarboxylic acid has potent anti-angiogenic activity and may be used for new therapeutic approaches for diseases of neovascularization including the treatment of solid tumors, diabetic retinopathy and arthritis, among others.

4 Claims, 1 Drawing Sheet

OTHER PUBLICATIONS

Ornitz, D. M. et al. "Heparin is Required for Cell-free Binding of basic Fibroblast Growth Factor to a Soluble Receptor and for Mitogenesis in Whole Cells", *Molecular and Cellular Biology,* vol. 12, (Jan. 1992) pp. 240–247.

Risaue, W. "Angiogenic Growth Factors", *Progress in Growth Factor Research,* vol. 2, (1990) pp. 71–79.

Schols, D. et al. "Specific Interaction of Aurinitricarboxylic Acid with the Human Immunodeficiency Virus/CD4 Cell Receptor", *Proc. Natl. Acad. Sci.* USA, vol. 86, (May 1989) pp. 3322–3326.

Skidmore, A. F. et al. "Characterization and Use of the Potent Ribonuclease Inhibitor Aurintricarboxylic acid for the Isolation of RNA from Animal Tissues", *Biochem. J.,* vol. 263, (1989) pp. 73–80.

Strony, J. et al. "Autrinicarboxylic Acid in a Canine Model of Coronary Artery Thrombosis", *Circulation,* vol. 81, No. 3, (Mar. 1990) pp. 1106–1114.

Weisz, P. B. et al. "Angiogenesis and Heparin Mimics", *Angiogenesis Key Principles—Science—Technology—Medicine,* (eds. R. Steiner, P. B. Weisz & R. Langer), (1992) pp. 107–117.

Woltering, E. A. et al. "Somatostatin Analogues Inhibit Angiogenesis in the Chick Chorioallantoic Membrane", *Journal of Surgical Research,* vol. 50 (1991) pp. 245–251.

*The Merck Index,* (1989) §899 p. 140.

*The Merck Index,* (1989) §4571 p. 735.

*The Merck Index,* (1989) §8986 p. 1423.

Takigawa, M. et al. "Tumor Angiogenesis and Polyamines: α-Difluoromethylornthine, an Irreversible Inhibitor of Ornithine Decarboxylase, Inhibitors B16 Melanoma-induced Angiogenesis in Ovo and the Proliferation of Vascular Endothelial Cells in Vitro", *Cancer Research,* vol. 50, (Jul. 1, 1990) pp. 4131–4138.

METHOD FOR INHIBITING ANGIOGENESIS WITH AURINTRICARBOXYLIC ACID, ITS ANALOGUES OR SALTS

TECHNICAL FIELD

This invention relates to the discovery that aurintricarboxylic acid has potent anti-angiogenic properties and activity and thus may be used for new therapeutic approaches for diseases of neovascularization including the treatment of solid tumors, diabetic retinopathy and arthritis, among others.

BACKGROUND ART

U.S. Pat. No. 4,007,270 to Bernstein et al. discloses that aurintricarboxylic acid (ATA) and certain of its derivatives and salts are useful as complement inhibitors which play an important role as mediators in immune, allergic, immunochemical and immunopathological reactions. The patent discloses a method of inhibiting the complement system in blood serum subjecting the serum to aurintricarboxylic acid or its derivatives or salts and that ATA has anti-inflammatory properties.

U.S. Pat. No. 4,880,788 to Moake et al. discloses a method for preventing and treating thrombosis. Moake et al. suggest that aurintricarboxylic acid may prevent yon Willebrand Factor mediated aggregation or agglutination of platelets and thereby prevents for formation of thromboemboli.

Cushman, M. et al. "Preparation and Anti-HIV Activities of Aurintricarboxylic Acid Fractions and Analogues: Direct Correlation of Antiviral Potency with Molecular Weight", *J. Med. Chem.*, Volume 34, (1991) pp. 329–337, disclose that aurintricarboxylic acid (ATA) binds to small gp120 in the absence of CD4 binding and is sufficient for anti-HIV activity.

Cushman, M. et al., "Synthesis and Anti-HIV Activities of Low Molecular Weight Aurintricarboxylic Acid Fragments and Related Compounds", *J. Med. Chem.*, Volume 34, (1991) pp. 337–342, disclose derivatives of aurintricarboxylic acid and their ability to afford protection against the cytopathogenicity of HIV-2 in MT-4 cell and HIV-1 in CEM cells. Two derivatives of ATA were found to inhibit syncytium formation. In contrast to ATA itself, two of the derivatives of ATA were inactive when tested for prevention of the binding of the OKT4A monoclonal antibody to the CD4 receptor and also for the inhibition of HIV-1 reverse transcriptase. It was concluded by Cushman et al. that these derivatives appear to act by a mechanism that is distinct from that of polymeric ATA. Cushman et al. do not disclose a method of use of aurintricarboxylic acid or its analogues or derivatives as an anti-angiogenic agent.

Gonzalez, R. G. et al. "Fractionation and Structural Elucidation of the Active Components of Aurintricarboxylic Acid, a Potent Inhibitor of Protein Nucleic Acid Interactions". *Biochimica et Biophysica Acta*, Volume 562, (1979) pp. 534–545, disclose that the triphenylmethane dye, aurintricarboxylic acid, is a potent inhibitor of protein-nucleic acid interactions. Gonzalez et al. noted that the degree of inhibitory activity of the aurintricarboxylic acid preparation depends on the degree of polymerization of the aurintricarboxylic acid polymer. The experimentation examined the ability of three fractions of ATA to inhibit DNA-poly L-lysine complex formation. Two biologically relevant assays were used based on the binding of polyribouridylic acid to ribosomal S1 and to *E. coli* 70-S ribosomes. The Gonzalez et al. publication noted that studies have eluded to the variable activity of commercial ATA preparations and that the commonly accepted structure of ATA might not be the true inhibitor of protein-nucleic acid interactions.

Mellon, W. S "Inhibitory Action of Aurintricarboxylic Acid and Rifamycin AF/013 at the Polynucleotide Domain of 1,25-Dihydroxyvitamin $D_3$-Receptor Complexes", *Biochemical Pharmacology*, Volume 33, Number 7, (1984) pp. 1047–1057, discloses that the binding of 1,25-dihydroxyvitamin $D_3$-receptor complexes from chicken intestine to DNA-cellulose and isolated intestinal nuclei is inhibited in a dose-dependent manner by ATA and rifamycin AF/013, which are known polymerase inhibitors. Mellon concluded that the observed inhibition was caused by ATA directly inhibiting the receptor. Mellon suggests that the receptor and polymerases have corresponding properties, but states that the question remains whether this is an insubstantial similarity or it is structurally relevant to hormone action.

Moudgil, V. K. et al. "Modulation of DNA Binding of Glucocorticoid Receptor by Aurintricarboxylic Acid", *J. Steroid Biochem.*, Volume 23, Number 2, (1985) pp. 125–132, disclose that ATA is an inhibitor of the DNA-binding of rat liver glucocorticoid-receptor complex. They found that treatment with ATA did not appear to alter the steroid binding properties of the receptor or accelerate dissociation of the complex. Moudgil et al. concluded that ATA does not inhibit the process of receptor activation and that it may act via interaction with the DNA-binding sites at the glucocorticoid-receptor. They suggest that the interaction may result in an alteration in the conformation of the activated receptor to a form unfavorable for optimum DNA-binding. They suggest that the skeletal structure of triphenylmethane, rather than the side chains, is the site of inhibitory action of ATA. Moudgil et al. reserve that the evidence presented in their study only indirectly argues in favor of an interaction between ATA and the glucocorticoid-receptors and that further studies are required to confirm the interaction.

Nakane, H. et al. "Differential Inhibition of various Deoxyribonucleic Acid Polymerases by Evans Blue and Aurintri-carboxylic Acid", *Eur. J. Biochem.*, Volume 177, (1988) pp. 91–96, disclose that both Evans blue and ATA exhibited inhibitor effects on the in vitro activity of all DNA polymerases, including human DNA polymerases, $\alpha$, $\beta$, $\tau$, DNA primase, calf-thymus terminal deoxynucleotidyltransferase, RLV reverse transcriptase, *E. coli* DNA polymerase 1, and RNA polymerase.

Skidmore, A. F. et al. "Characterization and Use of the Potent Ribonuclease Inhibitor Aurintricarboxylic Acid for the Isolation of RNA from Animal Tissues", *Biochem. J.*, Volume 263, (1989) pp. 73–80, disclose studies of ATA which yield that it is very useful as an RNAase inhibitor.

Schols, D. et al., "Specific Interaction of Aurintricarboxylic Acid with the Human Immunodeficiency Virus/CD4 Cell Receptor", *Proc. Natl. Acad. Sci. USA*, Volume 86, (May 1989) pp. 3322–3326, disclose that ATA is a compound that affects a rapid and selective modulation of CD-4 receptor expression on T4+ cells without affecting the expression of other cell-surface markers. Schols et al. suggest that the exact mechanism by which ATA blocks a CD-4 receptor remains unknown but the anionic character of ATA suggests that ATA should be able to bind to lysine and/or arginine residues. Strony, J. et al. "Aurintricarboxylic Acid in a Canine Model of Coronary Artery Thrombosis", *Circulation*, Volume 81, Number 3, (March 1990) pp. 1106–1114, disclose that ATA is unique in its inhibition of glycoprotein Ib-mediated platelet adhesion and subsequent aggregation. Strony et al. suggest that platelet glycoprotein Ib-von Willebrand factor interactions are important during coronary occlusion and that ATA can inhibit coronary thrombosis associated with coronary constriction. Strony et al. do not state that the inhibition of coronary occlusion is due to anti-angiogenic properties of ATA.

Benezra, M. et al. "Reversal of Basic Fibroblast Growth Factor-mediated Autocrine Cell Transformation by Aromatic Anionic Compounds", *Cancer Research*, Volume 52, (Oct. 15, 1992) pp. 5656–5662, disclose that ATA binds to basic fibroblast growth factor. Benezra et al. disclose that a common feature of compounds such as ATA and other dyes is their ability to mimic many of the biological effects of heparin such as anti-coagulation, release of ECM-bound bFGF, inhibition of heparanase activity and interaction with lipoprotein lipase. The study suggests that the effect of ATA may not be due to the actual interaction with bFGF, suggesting that ATA may function by blocking the participation of bFGF in an intracellular autocrine pathway.

Kan, M. et al. "An Essential Heparin-binding Domain in the Fibroblast Growth Factor Receptor Kinase", *Science*, Volume 259, (Mar. 26, 1993) pp. 1918–1921, disclose that heparin or heparin-like heparan sulfate proteoglycans are necessary for activity of the heparin-binding fibroblast growth factor family. Heparin interacts independently of the FGF ligand with a specific sequence (K18K) in one of the immunoglobulin-like loops in the extracellular domain of the FGF receptor tyrosine kinase transmembrane glycoprotein. Kan et al. found that a synthetic peptide corresponding to the K18K inhibited heparin and heparin dependent FGF binding to the receptor.

Bouck, N. "Tumor Angiogenesis: The Role of Oncogenes and Tumor Suppressor Genes", *Cancer Cells*, Volume 2, Number 6, (June 1990) pp. 179–185, discloses that the progressive growth of solid tumors is strictly dependent on their ability to attract new blood vessels that will supply them with oxygen and essential nutrients. Angiogenesis has been shown to precede or accompany malignancy. The focus of Bouck's study was to confirm that suppressor gene loss can influence angiogenesis. Bouck conjectures that molecules produced by normal cells that block angiogenesis may be helpful in combating tumor growth and the molecules produced by tumor cells that promote angiogenesis may be useful targets for anti-tumor drugs.

Gagliardi, A. et al. "Inhibition of Angiogenesis by Suramin", *Cancer Research*, Volume 52, (Sep. 15, 1992) pp. 5073–5075, disclose the ability of suramin to inhibit anglogenesis in chick chorioallantoic membrane. Gagliardi et al. disclose that suramin alone inhibited anglogenesis, and potentiated the activity of angiostatic steroids. Weisz, P. B. et al., "Anglogenesis and Heparin Mimics", *Anglogenesis: Key Principles—Science—Technology—Medicine*, (eds. R. Steiner, P. B. Weisz & R. Langer), (1992) pp. 107–117, disclose that glycosaminoglycans, such as heparin, can modulate angiogenesis and that this modulation varies greatly among varying heparin production lots and thus in glycosaminoglycans of different chemical structure.

Folkman, J. et al. "Angiogenesis Inhibition and Tumor Regression Caused by Heparin or a Heparin Fragment in the Presence of Cortisone", *Science*, Volume 221, (Aug. 19, 1983) pp. 719–725, disclose the inhibitory effect of heparin-cortisone.

Allain et al., "Mise en evidence de l'action anti-inflammatoire de l'alumninon ou acide aurine triboxylique", C. R. Seances Soc. Biol. Fil, Volume 174, (1980) pp. 68–73, disclose that aurintricarboxylic acid reduces Freund adjuvant-induced arthritis and carageen-induced oedemas in the paws of rats. Allain et al. do not disclose that aurintricarboxylic acid has anti-angiogenic properties but disclose the use of aurintricarboxylic acid as an anti-inflammatory agent for the treatment of arthritis.

DISCLOSURE OF THE INVENTION

It is an object of the present invention to provide a method for use of aurintricarboxylic acid, its analogues, salts and derivatives as anti-angiogenic agents or inhibitors of angiogenesis.

It is another object of the present invention to provide a method for the treatment of diseases which are anglogenesis-dependent such as the treatment of solid tumors, diabetic retinopathy, arthritis, for example.

It is another object of the present invention to provide a pharmaceutical composition for the treatment of diseases which are angiogenesis-dependent diseases.

A further object of the present invention provides a method of inhibiting anglogenesis using a compound which is not mitogenic to cells of an animal.

DESCRIPTION OF THE INVENTION

Figure 1:
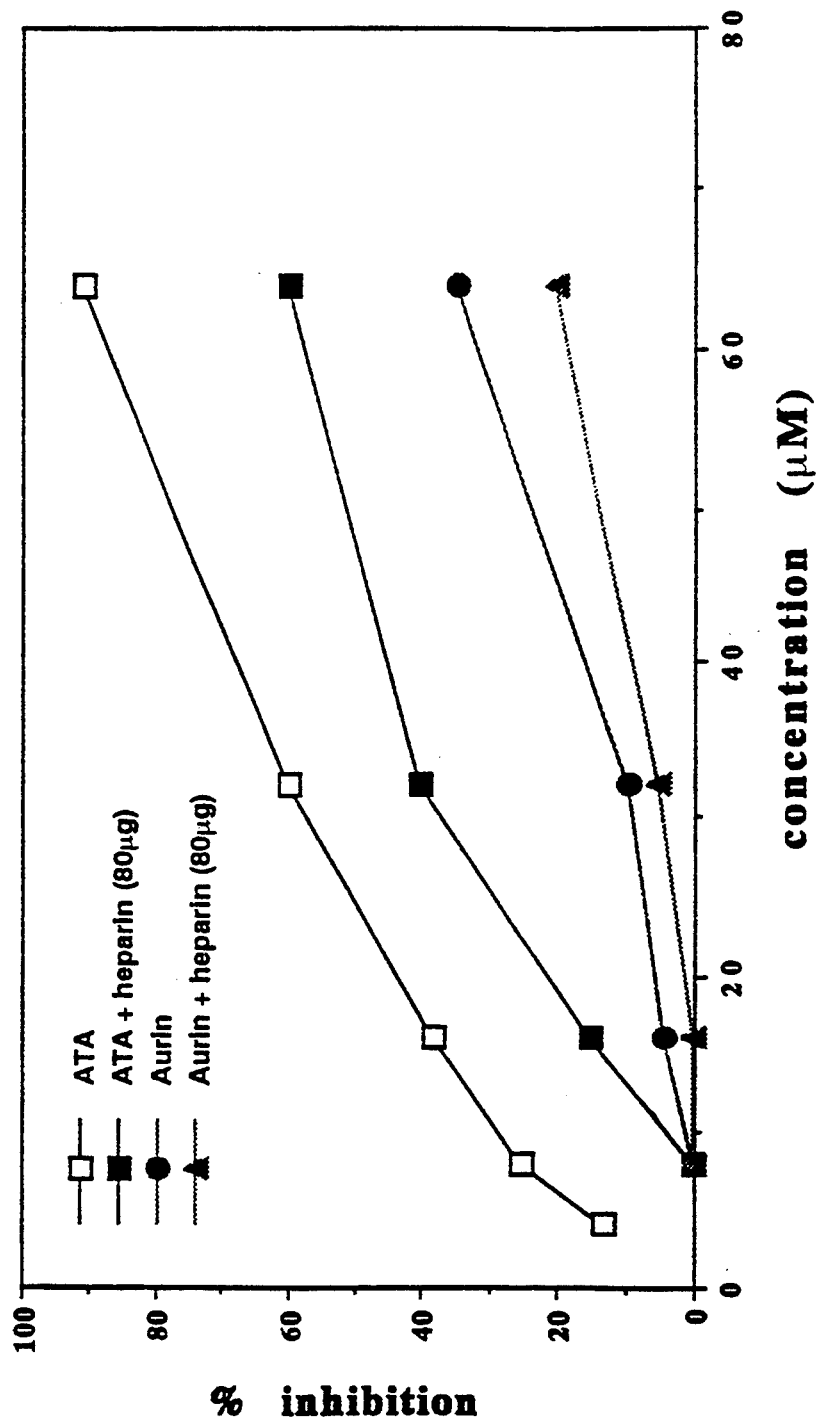
FIG. 1 shows the percentage of inhibition of anglogenesis due to increasing amounts of aurintricarboxylic acid (ATA) and aurin, with and without heparin.

Anglogenesis is the formation of blood and lymph vessels. Angiogenesis dependent diseases include, but are not limited to, tumor growth and metastasis, diabetic retinopathy, neovascular glaucoma and rheumatoid arthritis.

Thus, there is a need for experimentation and discovery of compounds, pharmaceutical compositions and methods for the inhibition of angiogenesis.

It has now been discovered that the aurintricarboxylic acid compounds and compositions of this invention are useful in the inhibition of angiogenesis and thus in the treatment of diseases which are anglogenesis-dependent.

Standard angiogenesis assays are well known in the art. These assays include proliferation and migration studies using various cell lines, collagenase inhibition and an in vivo angiogenesis assay on chicken chorioallantoic membranes (CAM) (see Auerbach, *Dev. Biol.* (1974) 41:391; and Crum, *Science*, Volume 230, (1985) p. 1375).

The chorioallantoic membrane of the chick embryo is often used as a semi-quantitative bioassay of angiogenic activity. The assay is quick and inexpensive and permits continuous, serial observations of changes in blood vessel growth. The rapid vascular growth of the CAM makes it an ideal model for observing modulation of angiogenesis, since sustained release implants containing specific test substances can be placed on the growing capillary network of the CAM (see Woltering et al. 1991. "Somatostatin analogues Inhibit Angiogenesis in the Chick Chorioallantoic Membrane", *Journal of Surgical Research,* 50: 245–251; and Oikawa et al. 1989. *Cancer Letters,* 48:157–162). The CAM assay is preferentially employed for searching for anti-angiogenic substances. The CAM model has been used to assay tumor related angiogenesis.

It is widely accepted that human and animal tumors can induce endothelial cell mitosis and anglogenesis, resulting in extensive neovascularization. Thus, angiogenic activity is critical for tumor implantation and subsequent growth. It has been shown that in the absence of neovascularization that the size of tumor grafts becomes limited. It is also known that neovascularization is essential for tumor growth, development, and metastasis; furthermore, when angiogenesis is absent, tumors tend to remain dormant (see Woltering et al., supra). Therefore, angiogenic activity has been directly correlated with tumor growth.

A variety of non-neoplastic diseases, previously thought to be unrelated, can be considered "angiogenic diseases" because they are dominated by the pathological growth of capillary blood vessels. These diseases include diabetic retinopathy, arthritis, hemangiomas, psoriasis, and ocular neovascularization, for example.

There seems to be little or no biochemical difference between angiogenic peptides expressed by tumors and those expressed by normal tissues. Nor are there any morphological differences between the new capillaries that respond to a malignancy and the capillary growth that occurs during physiological neovascularization (see Folkman et al. 1987. "Angiogenic Factors", *Science,* 235: 442–447).

As there is no qualitative difference between the angiogenic capabilities of nonmalignant and malignant diseases, results from normal and malignant vascularization assays can be easily compared, and progress can be made in either area independently of the system of investigation used (see Paweletz et al. 1989. "Tumor-related Angiogenesis", *Critical Reviews in Oncology/Hematology,* Volume 9, Issue 3, p. 197–198; and Takigawa et al. 1990. "Tumor Angiogenesis and Polyamines: a-Difluoromethylornithine, and Irreversible Inhibitor of Ornithine Decarboxylase, Inhibits B16 Melanoma-Induced Angiogenesis in Ovo and the Proliferation of Vascular Endothelial Cells in vitro", *Cancer Research,* 50: 4131–4138).

In addition, Glaser et al. have found that cultured human retinal pigment epithelial cells release a substance which, when applied to the CAM, causes regression of new blood vessels and also inhibits the proliferation of bovine endothelial cells in vitro. Thus, the CAM assay is an acceptable assay for diabetic retinopathy (Glaser et al., 1983. "Retinal Pigment Epithelial Cells release inhibitors of neovacularization", *Ophthalmology,* 94: p. 780).

Therefore, it is readily understood by one of ordinary skill in the art that an in vivo CAM assay showing the anti-angiogenic properties of ATA can readily be correlated to human treatments of angiogenesis-dependent diseases, such as tumor growth, diabetic retinopathy and arthritis.

Aurintricarboxylic acid (ATA) is a heterogeneous mixture of polymers that forms when salicylic acid is treated with formaldehyde, sulfuric acid and sodium nitrite (see Cushman, M. et al. "Preparation and Anti-HIV Activities of Aurintricarboxylic Acid Fractions and Analogues: Direct Correlation of Antiviral Potency with Molecular Weight", *J. Med. Chem.,* Volume 34, (1991) pp. 329–337; Cushman, M. et al. "Synthesis and Anti-HIV Activities of Low Molecular Weight Aurintricarboxylic Acid Fragments and Related Compounds", *J. Med. Chem.,* Volume 34, (1991) pp. 337–342).

Aurintricarboxylic acid is generally known to have the formula as set forth below:

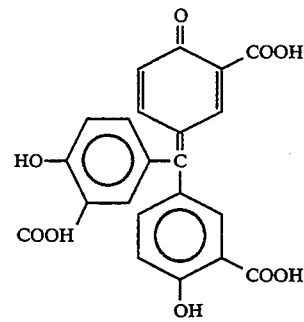

The heterogeneous mixture of ATA has been shown to inhibit protein nucleic acid interactions (Gonzalez, R. G. et al. "Fractionation and Structural Elucidation of the Active Components of Aurintricarboxylic Acid, a Potent Inhibitor of Protein Nucleic Acid Interactions", *Biochimica et Biophysica Acta,* Volume 562, (1979) pp. 534–545); to interact with steroid receptors at the nuclear uptake and the nuclear binding levels (Mellon, W. S., "Inhibitory Action of Aurintricarboxylic Acid and Rifamycin AF/013 at the Polynucleotide Domain of 1,25-Dihydroxyvitamin $D_3$-Receptor Complexes", *Biochemical Pharmacology,* Volume 33, Number 7, (1984) pp. 1047–1057; Moudgil, V. K. et al., "Modulation of DNA Binding of Glucocorticoid Receptor by Aurintricarboxylic Acid", *J. Steroid Biochem.,* Volume 23, Number 2, (1985) pp. 125–132); to inhibit DNA polymerase (Nakane, H. et al. "Differential Inhibition of various Deoxyribonucleic Acid Polymerases by Evans Blue and Aurintri-carboxylic Acid", *Eur. J. Biochem.,* Volume 177, (1988) pp. 91–96); and to act as a RNAase inhibitor (Skidmore, A. F. et al. "Characterization and Use of the Potent Ribonuclease Inhibitor Aurintricarboxylic acid for the Isolation of RNA from Animal Tissues", *Biochem. J.,* Volume 263, (1989) pp. 73–80).

ATA is a nonsulfated negatively-charged aromatic mixture of polymers that competes with heparin sulfate for binding to bFGF. ATA has been shown to reverse the transformed phenotype of sp bFGF transformed cells (cells transfected with a chimeric signal peptide-FGF) in terms of cell proliferation rate, morphological appearance and adhesive properties (Benezra, M. et al. "Reversal of Basic Fibroblast Growth Factor-mediated Autocrine Cell Transformation by Aromatic Anionic Compounds", *Cancer Research,* Volume 52, (Oct. 15, 1992) pp. 5656–5662). The capacity of ATA to interfere with the bFGF autocrine loop suggests important therapeutic potential in neoplastic diseases.

ATA is also a selective marker molecule for the immunodeficiency virus/CD4 receptor (Schols, D. et al. "Specific Interaction of Aurintricarboxylic Acid with the Human Immunodeficiency Virus/CD4 Cell Receptor", *Proc. Natl. Acad. Sci. USA,* Volume 86, (May 1989) pp. 3322–3326).

It inhibits platelet dependent thrombus formation (Strony, J. et al. "Aurintricarboxylic Acid in a Canine Model of Coronary Artery Thrombosis", *Circulation*, Volume 81, Number 3, (March 1990) pp. 1106–1114), and reverts basic fibroblast growth factor (bFGF) mediated autocrine cell transformation. Recent studies suggest that the interaction of bFGF with cell surface heparin sulfate is required for subsequent binding to high affinity cell surface receptors and signal transduction (Benezra, M. et al. "Reversal of Basic Fibroblast Growth Factor-mediated Autocrine Cell Transformation by Aromatic Anionic Compounds", *Cancer Research*, Volume 52, (Oct. 15, 1992) pp. 5656–5662).

Members of the FGF family are characterized by their high affinity for glycosaminoglycan and heparin, and their high mitogenicity for mesoderm and neuroectoderm derived cells. Furthermore, they are among the most potent inducers of neovascularization (see Kan, M. et al., "An Essential Heparin-binding Domain in the Fibroblast Growth Factor Receptor Kinase", *Science*, Volume 259, (Mar. 26, 1993) pp. 1918–1921; Ornitz, D. M. et al. "Heparin is Required for Cell-free Binding of basic Fibroblast Growth Factor to a Soluble Receptor and for Mitogenesis in Whole Cells", *Molecular and Cellular Biology*, Volume 12, (January 1992) pp. 240–247; Klagsbrun, M. et al. "MINIREVIEW: A Dual Receptor System is Required for Basic Fibroblast Growth Factor Activity", *Cell*, pp. 229–231; Risau, W., "Angiogenic Growth Factors", *Progress in Growth Factor Research*, Volume 2, (1990) pp. 71–79; Bouck, N., "Tumor Angiogenesis: The Role of Oncogenes and Tumor Suppressor Genes", *Cancer Cells*, Volume 2, Number 6, (June 1990) pp. 179–185).

A series of negatively charged aromatic compounds which mimic many of the effects of heparin, including suramin and ATA, compete with FGF binding with heparin sulfate on the cell surface (Benezra, M. et al., "Reversal of Basic Fibroblast Growth Factor-mediated Autocrine Cell Transformation by Aromatic Anionic Compounds", *Cancer Research*, Volume 52, (Oct. 15, 1992) pp. 5656–5662). The ability of solid tumors to grow to a clinically significant size is dependent on angiogenesis (Kan, M. et al. "An Essential Heparin-binding Domain in the Fibroblast Growth Factor Receptor Kinase", *Science*, Volume 259, (Mar. 26, 1993) pp. 1918–1921. Stimulation of bFGF and the vasculotropin/endothelial cell growth factor is a critical event in angiogenesis (Folkman, J. et al. "Anglogenesis Inhibition and Tumor Regression Caused by Heparin or a Heparin Fragment in the Presence of Cortisone", *Science*, Volume 221, (Aug. 19, 1983) pp. 719–725).

Growth factors have been shown to be displaced from their receptors by suramin (Benezra, M. et al. "Reversal of Basic Fibroblast Growth Factor-mediated Autocrine Cell Transformation by Aromatic Anionic Compounds", *Cancer Research*, Volume 52, (Oct. 15, 1992) pp. 5656–5662), and it has been recently shown that suramin is a potent inhibitor of angiogenesis (Gagliardi, A. et al., "Inhibition of Angiogenesis by Suramin", *Cancer Research*, Volume 52, (Sep. 15, 1992) pp. 5073–5075).

ATA may mimic many of the actions of heparin without being mitogenic to endothelial cells (Weisz, P. B. et al. "Anglogenesis and Heparin Mimics", *Angiogenesis: Key Principles—Science—Technology—Medicine*, (eds. R. Steiner, P. B. Weisz & R. Langer), (1992) pp. 107–117). Folkman et al. (Folkman, J. et al. "Angiogenesis Inhibition and Tumor Regression Caused by Heparin or a Heparin Fragment in the Presence of Cortisone", *Science*, Volume 221, (Aug. 19, 1983) pp. 719–725) showed that heparin and heparin fragments without anticoagulant activity inhibited angiogenesis in the presence of cortisol, 17α-hydroxyprogesteroneandtetrahydrocortisol.

Experimentation was performed to determine the ability of aurintricarboxylic acid, its salts, derivatives and analogues to inhibit anglogenesis in the chick chorioallantoic membrane.

The example set forth below demonstrates the dose dependent inhibition of angiogenesis by ATA. In addition, the interaction of ATA with heparin and angiostatic steroids is described.

EXAMPLE 1

Materials and Methods

Aurintricarboxylic acid trisodium salt and aurin were obtained from Aldrich Chemical Company, Milwaukee, Wis. Procedures for the synthesis of aurintricarboxylic acid are reported (see Heisig, G. B. and Lauer, W. M. Org. Syn., Volume 9, (1928) p. 54–55.) Aurintricarboxylic acid was also obtainable from Fischer Scientific Co., Sigma Chemical Company, and Mallinkrodt Chemical Co. (See Gonzalez, R. G. et al. "Fractionation and Structural Elucidation of the Active Components of Aurintricarboxylic Acid, a Potent Inhibitor of Protein Nucleic Acid Interactions", *Biochimica et Biophysica Acta*, Volume 562, (1979) pp. 534–545).

Heparin sodium USP (PM-20487, activity 171 U/mg) was a gift from Dr. Judah Folkman, Boston, Mass. The steroids were obtained from Sigma Chemical Co., St. Louis, Mo. or Steraloids, Inc., Wilton, N.H. All other chemicals were of reagent grade. Fertilized eggs (SPF grade) were obtained from Sunrise Farms (Catskill, N.Y.).

The ability of suramin compounds to inhibit angiogenesis was determined as previously described (Gagliardi, A. et al., "Inhibition of Angiogenesis by Suramin,", *Cancer Research*, Volume 52, (1992) pp. 5073–5075), using a modification of the chick chorioallantoic membrane (CAM) assay (Crum, R. et al., "A New Class of Steroids Inhibits Angiogenesis in the Presence of Heparin or a Heparin Fragment", *Science* (Washington, D.C.), Volume 230, (1985) pp. 1375–1378). The eggs were cracked on day 3 and the embryos placed in petri dishes in a humidified $CO_2$ incubator (3% $CO_2$/air) at 37° C. Each compound or combination of compounds to be tested were dissolved in methylcellulose (0.45%) and the solution (10 μl) was air-dried on a Teflon-coated metal tray. The methylcellulose disk was implanted on the outer third of a day 6 CAM where capillaries were still growing. The disk alone and cortisol-21-phosphate (100 μg) plus heparin (80 μg) were used as negative and positive controls, respectively. The zone around the disk was examined 48 hours after implantation and inhibition of anglogenesis was indicated by an avascular zone of ≧4 mm diameter around the disk. At least 20 embryos were measured for each compound or combination of compounds. The results were expressed as the percentage of embryos which showed inhibition of angiogenesis.

The vessels of the CAM preparation grew rapidly until day 10, after which endothelial proliferation decrease sharply (Ausprunk, D. R. et al., *Developmental Biology*, Volume 38, (1974) p. 237; Folkman, J. et al. "Angiogenesis Inhibition and Tumor Regression Caused by Heparin or a Heparin Fragment in the Presence of Cortisone", *Science*, Volume 221, (1983) pp. 719-725). The effects of drug treatment on established vessels with low angiogenic activity were also determined by implanting the compound or combination of compounds to be tested on day 13 and determining the percentage of embryos showing inhibition of angiogenesis on day 15 (late implants).

The effects of increasing amounts of ATA, aurin and aurin plus heparin on the inhibition of angiogenesis are shown in Table 1 and FIG. 1 below. ATA clearly inhibited angiogenesis when 4 μg were added to the disk (35% inhibition), and the inhibition increased in a dose related manner to 91% when 32 μg of ATA were added. On the other hand, aurin showed much lower activity with 35% inhibition when 20 μg (molar equivalent to 32 μg of ATA) were added to the disk.

The angiostatic activity by ATA was reduced in the presence of 80 μg of heparin. This inhibition of the angiostatic activity of ATA was partially overcome by increasing the concentration of ATA in the disk (Table 1, FIG. 1). On the other hand, the angiostatic activity by aurin was not significantly changed in the presence of heparin (Table 1, FIG. 1 below).

Table 2 below shows the percentage inhibition of angiogenesis by several steroids either alone or in the presence of heparin or ATA. None of the steroids studied showed significant inhibitory activity alone under the condition of the CAM assay. All the steroids examined (cortisol-21-phosphate, 17-α-hydroxyprogesterone, tetrahydrocortexolone and tetrahydrocortisol) exhibited significant inhibition of angiogenesis in the presence of 8 μg of ATA.

Table 3 below shows the results for disks implanted on day 13. ATA clearly exhibited angiostatic activity with 85% inhibition at a concentration of 32 μg. Aurin alone showed much less angiostatic activity with 10% inhibition at an equivalent molar concentration. Only ATA and suramin exhibited angiostatic activity in both the early and late CAM preparation. Neither cortisol-21-phosphate, tetrahydrocortisol, tetrahydrocortexolone nor 17α-hydroxyprogesterone in the presence of heparin nor tamoxifen, clomifene and ICI 182,780 alone showed angiostatic activity in the late CAM.

The results of these experiments clearly show that ATA is a potent inhibitor of angiogenesis in the CAM. Furthermore, the inhibition of angiogenesis is dose dependent, increasing from 25% inhibition with 4 μg of ATA to 91% inhibition at 32 μg. The angiostatic activity of ATA is not dependent on the presence of heparin. Thus, ATA seems to be similar to, but more potent, than suramin in its anti-angiogenic activity (Gagliardi, A. et al., "Inhibition of Angiogenesis by Suramin", *Cancer Research*, Volume 52, (Sep. 15, 1992) pp. 5073-5075).

An additional finding from the above example is the antagonism between ATA and heparin. The multiple sulfate groups on heparin complex with molecules containing cationic centers, such as cationic dyes and peptides/proteins with neighboring basic amino acid residues (including FGF) (Weisz, P. B. et al., "Angiogenesis and Heparin Mimics", *Angiogenesis: Key Principles—Science—Technology—Medicine*, (eds. R. Steiner, P. B. Weisz & R. Langer), (1992) pp. 107-117). In angiogenesis and endothelial cell growth promotion, heparin-like substances complex to bFGF, the cell surface and to the extracellular matrix, thereby enhancing mitogenicity.

Aurintricarboxylic acid showed potent anti-angiogenic activity in a dose related manner. In the presence of heparin, the anti-angiogenic activity of aurintricarboxylic acid was decreased. Aurintricarboxylic acid also potentiated the activity of the angiostatic steroids such as cortisol-21-phosphate, 17-α-hydroxyprogesterone, tetrahydrocortexolone and tetrahydrocortisol.

The above results indicate that ATA may effectively replace heparin as an activator of angiostatic steroids (Table 2 below). We have previously shown (Gagliardi, A. et al., "Inhibition of Angiogenesis by Suramin", *Cancer Research*, Volume 52, (1992) pp. 5073-5075) that suramin can inhibit angiogenesis in the CAM preparation. In addition, the anti-angiogenic activity of suramin is antagonized by heparin. ATA, at concentrations 10 fold lower than suramin, expressed a similar inhibitory activity on angiogenesis.

The structures of ATA, suramin and heparin show important differences in chemical structure. The most notable difference being that the major polyanionic group in heparin and suramin is sulfonate, whereas ATA contains carboxylate groups. Both suramin and ATA contain aromatic rings lined via enzyme resistant methylene groups, while heparin has a sugar backbone. The molecular weights of these compounds are vastly different. The heparin used in these studies had a molecular weight of 20,487, suramin had a molecular weight of 1,430 and ATA (although being a heterogenous mixture) had an estimated molecular weight of around 3,000-5,000 (Cushman, M. et al., "preparation and Anti-HIV activities of aurintricarboxylic acid fractions and analogues: direct correlation of antiviral potency with molecular weight", *J. Med. Chem.*, Volume 34, (1991) pp. 329-337). The presence of the carboxylic groups on ATA is considered to be important for angiostatic activity because aurin, a chemically related compound without the tricarboxylic residues, exhibits low anti-angiogenic activity.

The inhibitory effects of ATA and suramin in the 13-day CAM preparation when FGF level in the CAM fluid is very low suggest that these compounds may affect blood vessels by mechanisms other than blocking bFGF action on endothelial cell growth.

These novel findings suggest that aurintricarboxylic acid provides the basis for important new therapeutic approaches for diseases of neovascularization.

Thus, the invention relates to a method comprising inhibiting angiogenesis by administering an effective amount of aurintricarboxylic acid, its analogues, derivatives or salts. The invention comprises a method for the treatment of angiogenesis-dependent diseases by administering an effective amount of aurintricarboxylic acid, its analogues, derivatives or salts to a patient. Angiogenesis dependent diseases include, but are not limited to diabetic retinopathy, arthritis, tumor growth and metastasis and neovascular glaucoma. Treatments may include an effective amount which comprises about 10 mg/kg/day of aurintricarboxylic acid.

In an alternative embodiment, the method for inhibiting angiogenesis includes administering an effective amount of a composition comprising aurintricarboxylic acid, its analogues, derivatives or salts and asteroid composition to an animal. The steroid composition may be selected from the group consisting of cortisol-21-phosphate, 17-α-hydroxyprogesterone, tetrahydrocortexolone and tetrahydrocortisol or mixtures thereof.

The invention includes a pharmaceutical composition for the inhibition of angiogenesis comprising an angiogenesis inhibiting amount of aurintricarboxylic acid and a steroid composition selected from the group consisting of cortisol-21-phosphate, 17-α-hydroxyprogesterone, tetrahydrocortexolone and tetrahydrocortisol.

Compounds of the present invention have anti-angiogenic properties in animals. Compounds of the present invention and compositions which are shown to have physiological effects of inhibiting angiogenesis find use in numerous therapeutical applications, such as the treatment of angiogenesis-dependent diseases, including diabetic retinopathy, arthritis, tumor growth and metastasis and neovascular glaucoma.

Therapeutic compositions comprise an effective amount of the compounds of the invention including non-toxic addition salts. Such compositions can also be provided together with physiologically tolerable liquid, gel or solid diluents, adjuvants and excipients.

These compositions can be administered to animals for veterinary use, such as with domestic animals and clinical use in humans in a manner similar to other therapeutic agents. In general, the dosage required for therapeutic efficacy will range from about 1 μg to 300 mg/kg, preferably 10 μg to 30 mg/kg of the host body weight, and more preferably about 6.7 mg/kg or 10.0 mg/kg of host body weight of aurintricarboxylic acid. Alternatively, dosages within these ranges can be administered by constant infusion over an extended period of time, usually exceeding 24 hours, until the desired therapeutic benefits have been obtained. The chemical structure suggests that this compound will be efficiently absorbed from the gut. One may also deliver this material directly into the eye using implants of via an implant in or on the skin.

Typically such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing agents, or pH buffering agents, and the like.

The compositions are conventionally administered by injection, either subcutaneously or intravenously. Additional formulations which are suitable for other modes of administration include, suppositories, intranasal aerosol, and in some cases, oral formulations. For suppositories, traditional binders and excipients may include, for example, polyalkylene glycols or triglycerides: such suppositories may be formed from mixtures containing the active ingredient in the range of 0.5 to 10%, preferably 1-2%. Oral formulations include such normally employed excipients as, for example, pharmaceutical grades of mannitol, lactose, starch, magnesium stearate, sodium saccharine, cellulose, magnesium carbonate, and other conventional additives. These compositions take the form of solutions, suspensions, tablets, pills, capsules, sustained release formulations or powders and contain 10% to 90% of the active ingredient, preferably 25% to 70%. These oral formulations are designed to protect the activity of the aurintricarboxylic acid composition or its derivative or analogue until it can be absorbed.

The aurintricarboxylic acid compositions of the invention can be formulated into the compositions as neutral or salt forms. Pharmaceutically acceptable non-toxic salts include the acid addition salts, for example, hydrochloric or phosphoric acids or such organic acids as ascetic, oxalic, tartaric, mandelic, etc. Salts formed with free carboxyl groups may be derived from inorganic bases such as, for example, sodium, potassium, ammonium, calcium or ferric hydroxides. Tissue culture experiments show that ATA binds basic fibroblast growth factor at pH 6.5–7.5. (Benezra, M. et al., "Reversal of basic fibroblast growth-mediated autocrine cell transformation by aromatic anionic compounds", *Cancer Research*, Volume 52, (1992) pp. 5656–5662. Thus it is preferred that pharmaceutical compositions of the invention have a pH of about 6.5–7.5.

TABLE 1

Percentage of inhibition of angiogenesis for different amounts of Aurintricarboxylic acid (ATA) and Aurin alone and in combination with heparin. The number of embryos showing inhibition/total embryos evaluated (+/total) and the percentage showing inhibition (% of inhibition) are shown.

| COMPOUND | EMBRYOS (+/total) | % of Inhibition |
|---|---|---|
| Disk only | 0/25 | 0 |
| 2 μg ATA | 3/22 | 14 |
| 4 μg ATA | 5/20 | 25 |
| 8 μg ATA | 8/21 | 38 |
| 16 μg ATA | 12/20 | 60 |
| 32 μg ATA | 20/22 | 91 |
| 64 μg ATA | 23/23 | 100 |
| 1.25 μg Aurin | 0/20 | 0 |
| 2.50 μg Aurin | 0/24 | 0 |
| 5.00 μg Aurin | 1/23 | 4 |
| 10.00 μg Aurin | 2/21 | 10 |
| 20.00 μg Aurin | 10/29 | 35 |
| μg ATA | | |
| 2 + 80 μg heparin | 0/22 | 0 |
| 4 + 80 μg heparin | 0/21 | 0 |
| 8 + 80 μg heparin | 3/20 | 15 |
| 16 + 80 μg heparin | 8/20 | 40 |
| 32 + 80 μg heparin | 12/20 | 60 |
| 64 + 80 μg heparin | 17/21 | 81 |
| μg Aurin | | |
| 1.25 + 80 μg heparin | 0/22 | 0 |
| 2.50 + 80 μg heparin | 0/20 | 0 |
| 5.00 + 80 μg heparin | 0/22 | 0 |
| 10.00 + 80 μg heparin | 1/20 | 5 |
| 20.00 + 80 μg heparin | 4/20 | 20 |

TABLE 2

Percentage of Inhibition of Angiogenesis for Angiostatic Steroids alone or in the presence of 100 μg of heparin or increasing amounts of aurintricarboxylic acid (ATA). The number of embryos showing inhibition/total embryos evaluated (+/total) and the percentage showing inhibition (% of inhibition) are shown.

| COMPOUND | EMBRYOS (+/total) | % of Inhibition |
|---|---|---|
| 100 μg cortisol-21-phosphate only | 8/29 | 26 |
| +2 μg ATA | 8/22 | 36 |
| +4 μg ATA | 10/20 | 50 |
| +8 μg ATA | 18/21 | 86 |
| +16 μg ATA | 20/21 | 95 |
| +32 μg ATA | 23/23 | 100 |
| +80 μg heparin | 27/41 | 66 |
| 100 μg 17α-hydroxyprogesterone only | 0/54 | 0 |
| +2 μg ATA | 11/23 | 48 |
| +4 μg ATA | 16/20 | 69 |
| +8 μg ATA | 22/23 | 95 |
| +80 μg heparin | 26/58 | 45 |
| 100 μg tetrahydrocortisol only | 0/53 | 0 |
| +2 μg ATA | 8/22 | 36 |
| +4 μg ATA | 13/22 | 59 |

TABLE 2-continued

Percentage of Inhibition of Angiogenesis for Angiostatic Steroids alone or in the presence of 100 μg of heparin or increasing amounts of aurintricarboxylic acid (ATA). The number of embryos showing inhibition/total embryos evaluated (+/total) and the percentage showing inhibition (% of inhibition) are shown.

| COMPOUND | EMBRYOS (+/total) | % of Inhibition |
|---|---|---|
| +8 μg ATA | 22/25 | 88 |
| +80 μg heparin | 17/38 | 45 |
| 100 μg medroxyprogesterone acetate only | 0/59 | 0 |
| +2 μg ATA | 9/21 | 43 |
| +4 μg ATA | 13/23 | 56 |
| +8 μg ATA | 14/20 | 70 |
| +80 μg heparin | 0/24 | 0 |
| 80 μg heparin only | 0/23 | 0 |

TABLE 3

Percentage of Inhibition of Angiogenesis for Several Compounds Implanted on the Late CAM (Day 13) and Early CAM (Day 6). The number of embryos showing inhibition/total embryos evaluated (+/total) and the percentage showing inhibition (% of inhibition) are shown.

| COMPOUND | LATE CAM % of Inhibition | LATE CAM EMBRYOS (+/total) | EARLY CAM % of Inhibition | EARLY CAM EMBRYOS (+/total) |
|---|---|---|---|---|
| Disk only | 0 | (0/25) | 0 | (0/23) |
| cortisol-21-PO$_4$ | 5 | (1/18) | 66 | (27/41) |
| (100 μg) + heparin (100 μg) | | | | |
| Clomiphene (100 μg) | 0 | (0/18) | 59 | (13/22) |
| Tamoxifen (100 μg) | 0 | (0/22) | 61 | (25/40) |
| ICI 182,780 (100 μg) | 0 | (0/19) | 80 | (24/30) |
| Suramin (100 μg) | 74 | (26/35) | 58 | (15/26) |
| ATA (32 μg) | 85 | (17/20) | 91 | (20/22) |
| Aurin (10 μg) | 10 | (2/20) | 35 | (10/29) |

Although the foregoing invention has been described in some detail by way of illustration and example for purposes of clarity and understanding, it will be obvious that certain changes and modifications may be practiced within the scope of the appended claims.

We claim:

1. A method for inhibiting angiogenesis in an animal comprising administering an effective amount to inhibit angiogenesis of aurintricarboxylic acid, its analogues, or salts to said animal.

2. A method according to claim 1, wherein said animal is a mammal or bird.

3. A method according to claim 1, wherein said effective amount comprises about 10 mg/kg body weight of the host of aurintricarboxylic acid.

4. A method according to claim 1, wherein said aurintricarboxylic acid has a molecular weight of about 3000 to 5000.

* * * * *